US012660902B2

(12) United States Patent
    Chen

(10) Patent No.: US 12,660,902 B2
(45) Date of Patent: Jun. 23, 2026

(54) ESSENTIAL OIL SPRAY DEVICE AND HAIR DRYER

(71) Applicant: Zhongshan Xinlijia Trading Co., Ltd, Zhongshan City (CN)

(72) Inventor: Chunlin Chen, Zhongshan City (CN)

( * ) Notice: Subject to any disclaimer, the term of this patent is extended or adjusted under 35 U.S.C. 154(b) by 326 days.

(21) Appl. No.: 18/434,800

(22) Filed: Feb. 6, 2024

(65) Prior Publication Data

US 2024/0172855 A1 May 30, 2024

(30) Foreign Application Priority Data

Nov. 10, 2023 (CN) .......................... 202323054964.8

(51) Int. Cl.
| | |
|---|---|
| *A45D 20/00* | (2006.01) |
| *A45D 19/16* | (2006.01) |
| *A45D 20/08* | (2006.01) |
| *A45D 20/10* | (2006.01) |
| *A45D 20/12* | (2006.01) |
| *A45D 34/04* | (2006.01) |
| *A61L 9/14* | (2006.01) |
| *A61M 11/04* | (2006.01) |
| *A61M 11/08* | (2006.01) |
| *B05B 7/00* | (2006.01) |
| *B05B 17/06* | (2006.01) |

(52) U.S. Cl.
    CPC ............. *A45D 20/00* (2013.01); *A45D 19/16* (2013.01); *A45D 20/08* (2013.01); *A45D 20/10* (2013.01); *A45D 20/12* (2013.01); *A45D 34/04* (2013.01); *A61L 9/14* (2013.01); *A61M 11/042* (2014.02); *A61M 11/08*

(2013.01); *B05B 7/0012* (2013.01); *B05B 17/0607* (2013.01); *B05B 17/0615* (2013.01); *A45D 2200/057* (2013.01); *A45D 2200/058* (2013.01); *A61L 2209/135* (2013.01)

(58) Field of Classification Search
    CPC ........ A45D 19/16; A45D 20/00; A45D 20/08; A45D 20/10; A45D 20/12; A45D 2200/057; A45D 2200/058; A61L 9/14; A61L 2209/135; A61M 11/042; A61M 11/08; B05B 7/0012; B05B 17/0607; B05B 7/0615
    USPC ......................................... 422/124
    See application file for complete search history.

(56) References Cited

U.S. PATENT DOCUMENTS

| | | | | |
|---|---|---|---|---|
| 2006/0064892 A1* | 3/2006 | Matsui | .................. | A45D 20/50 34/96 |
| 2019/0315538 A1* | 10/2019 | Cheng | ................ | B65D 81/3453 |
| 2020/0237950 A1* | 7/2020 | Xiao | .................... | A61M 11/042 |
| 2022/0175107 A1* | 6/2022 | Hsu | ........................ | A45D 20/12 |

(Continued)

*Primary Examiner* — Jason H Duger

(57) ABSTRACT

An essential oil spray device, including: a box assembly comprising a liquid storage part with a liquid filling port; a cover assembly, sealingly connected to the liquid storage part, wherein the cover assembly is provided with a spray port, and the spray port is provided with an atomizing member; a plug, provided at the liquid filling port; and a switch assembly, provided on the box assembly and electrically connected to the atomizing member. The essential oil spray device addresses deficiencies in the prior art, including the need to replace an essential oil bottle with a new essential oil bottle after the essential oil is used up, high use cost, and the need for an essential oil bottle housing that requires a complex structure and a large installation space.

8 Claims, 6 Drawing Sheets

(56) References Cited

U.S. PATENT DOCUMENTS

2023/0009980 A1 *   1/2023   Oikaze .................. B05B 7/0081
2025/0302173 A1 *   10/2025   Lam ...................... B05B 7/2489

* cited by examiner

1

ESSENTIAL OIL SPRAY DEVICE AND HAIR DRYER

CROSS-REFERENCE TO RELATED APPLICATION

This application claims priority to Chinese Patent Application No. 202323054964.8, filed on Nov. 10, 2023 before the China National Intellectual Property Administration, the disclosure of which is incorporated herein by reference in entirety.

TECHNICAL FIELD

The present disclosure relates to the field of hair care products, and in particular to an essential oil spray device and a hair dryer.

The hair dryer has been optimized in its function of drying hair. By adding an essential oil spray device, the hair dryer can spray essential oil onto the hair while blowing, and use essential oil to care for the hair.

BACKGROUND

Existing essential oil spray devices often use an essential oil bottle and a housing which are separated, that is, the essential oil bottle and the housing are detachably connected. Essential oil are stored in the essential oil bottle, when the essential oil is used up, it is generally necessary to replace it with a new essential oil bottle. The housing is provided with electrical components such as switches, which can control the atomizing member in the essential oil bottle to atomize and spray out the essential oil. This kind of essential oil spray device needs to be replaced with a new essential oil bottle after the essential oil is used up, the use cost is high, and the essential oil bottle and the housing adopt a split design, causing a complex structure and a large installation space.

SUMMARY

Therefore, the technical problem to be solved by the present disclosure is to overcome the defects of the essential oil spray device in the prior art, for example, it needs to replace the essential oil bottle with a new essential oil bottle after the essential oil is used up, the use cost is high, and the essential oil bottle and housing adopt a split design, causing a complex structure and a large installation space. Thereby it provides an essential oil spray device that replenishes essential oil without replacing essential oil bottle, reduces the cost of use, adopts an integral design, and has simple structure, and small installation space.

In order to solve the above problems, the present disclosure provides an essential oil spray device, including:

a box assembly comprising a liquid storage part, a liquid filling port being provided in the liquid storage part;

a cover assembly, sealingly connected to the liquid storage part, the cover assembly being provided with a spray port, and the spray port being provided with an atomizing member;

a plug, provided at the liquid filling port;

a switch assembly, provided on the box assembly and electrically connected to the atomizing member.

According to some embodiments of the present disclosure, the box assembly further comprises a connecting part, and the connecting part is arranged around the liquid storage part and connected with the liquid storage part.

According to some embodiments of the present disclosure, the connecting part has an annular groove, and a magnetic component is arranged in the annular groove.

According to some embodiments of the present disclosure, the cover assembly comprises an inner cover and an outer cover, the outer cover is sealingly connected with the liquid storage part, the spray port is provided on the outer cover, the inner cover is arranged inside the outer cover and connected with the outer cover.

According to some embodiments of the present disclosure, the atomizing member is provided between the outer cover and the inner cover, and the atomizing member is provided with seals on both sides thereof.

According to some embodiments of the present disclosure, the switch assembly comprises a first switch and a second switch provided on the connecting part, the first switch is electrically connected to the second switch, and the second switch is electrically connected to the atomizing member.

According to some embodiments of the present disclosure, the essential oil spray device further includes a power supply component, wherein the power supply component comprises a battery and a charging port disposed in the annular groove of the connecting part.

According to some embodiments of the present disclosure, the plug is made of fluorosilicone material.

According to another aspect of the present disclosure, there is provided a hair dryer, comprising the essential oil spray device according to any one of the above embodiments, wherein the essential oil spray device is arranged in a body of the hair dryer, and the spray port faces towards an air-out side of the body of the hair dryer.

According to some embodiments of the present disclosure, the essential oil spray device is magnetically connected to the body of the hair dryer through a magnetic component in the connecting part of the box assembly.

The present disclosure has the following advantages:

1. The essential oil spray device provided by the present disclosure includes: a box assembly, a cover assembly, a plug and a switch assembly. The box assembly includes a liquid storage part, essential oil is filled/placed in the liquid storage part, and the liquid storage part is provided with a liquid filling port, a plug is provided at the liquid filling port. The plug can be pulled out and essential oil can be added to the liquid storage part through the liquid filling port, after the addition is completed, the plug may be installed for sealing. The cover assembly is sealingly connected to the liquid storage part, the cover assembly is provided with a spray port, and an atomizing member is provided at the spray port. The switch assembly is provided on the box assembly and electrically connected to the atomizing member. The atomizing member can be controlled through the switch assembly to work, atomize the essential oil in the liquid storage part and spray it out from the spray port when needed. Since the essential oil can be added through the liquid filling port after use, there is no need to replace the entire unit, and the cost of use is low. Moreover, the overall structure is more compact and it takes up less installation space.

2. In the essential oil spray device provided by the present disclosure, the box assembly also includes a connecting part, the connecting part is arranged around the outside of the liquid storage part and connected with the liquid storage part. The connecting part has an annular groove, and a magnetic component is arranged in the annular groove. The essential oil spray device can be connected to a hair dryer through the magnetic component. This connection method is simple and fast, and is easy to disassemble and assemble.

3. In the essential oil spray device provided by the present disclosure, the cover assembly includes an outer cover and an inner cover. The atomizing member is arranged between the outer cover and the inner cover, and seals are provided on both sides of the atomizing member to achieve a complete sealing at the atomizing member, it has good sealing performance and prevents the essential oil in the liquid storage part from leaking.

4. In the essential oil spray device provided by the present disclosure, the switch assembly includes a first switch and a second switch provided on the connecting part. The first switch is electrically connected to the second switch, and the second switch is electrically connected to the atomizing member. When and only when both the first switch and the second switch are turned on, the essential oil spray device will work. When only one of them is turned on, the essential oil spray device will be in a standby state and will not spray out essential oil. By setting the first switch and the second switch, the essential oil spray device can be prevented from being opened due to misoperation.

5. In the essential oil spray device provided by the present disclosure, the power supply component includes a battery and a charging port arranged in the annular groove of the connecting part. The battery can be charged through the charging port, so that the essential oil spray device can be used continuously.

6. The plug of the essential oil spray device provided by the present disclosure is made of fluorosilicone material. This material will not expand under long-term immersion in the essential oil like ordinary silicone materials, and this material has good high temperature resistance, which can meet the usage requirements of the hair dryer under hot air conditions. The plug made of fluorosilicone material is more durable and has a long service life.

7. In the hair dryer provided by the present disclosure, the essential oil spray device is installed in the body of the hair dryer, and the spray port faces towards an air-out side of the body of the hair dryer. When the hair dryer blows, the essential oil atomized by the essential oil spray device can be carried and blown out to the hair, that is, the user can use essential oil to care for the hair and blow-dry the hair at the same time. Moreover, the essential oil spray device is magnetically connected to the body of the hair dryer through the magnetic component, making it easier and faster to disassemble and assemble.

BRIEF DESCRIPTION OF THE DRAWINGS

In order to more clearly explain the specific embodiments of the present disclosure or the technical solutions in the prior art, the drawings that need to be used in the description of the specific embodiments or the prior art will be briefly introduced below. Obviously, the drawings in the following description illustrate some embodiments of the present disclosure. For those of ordinary skill in the art, other drawings can be obtained based on these drawings without exerting creative efforts.

REFERENCE NUMERAL

Figure 1:
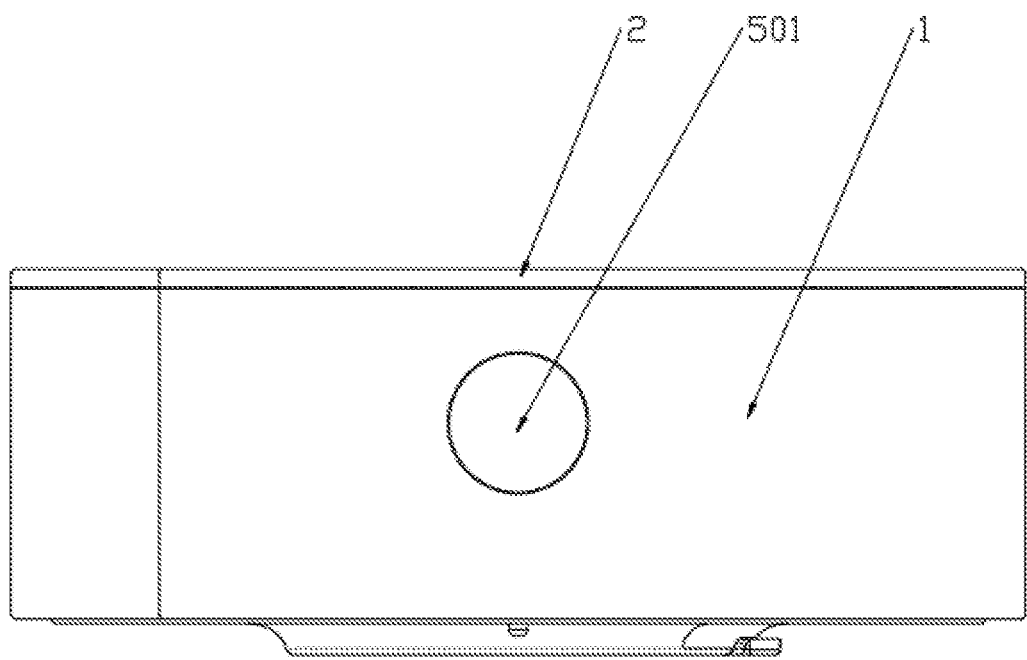
FIG. 1 is a schematic view of the essential oil spray device of the present disclosure.

1. Box assembly, 101. Liquid storage part, 102. Liquid filling port, 103. Connecting part, 104. Magnetic component;
2. Cover assembly, 201. Spray port, 202. Inner cover, 203. Outer cover, 204. Seal, 205. Sealing ring;
3. Atomizing member;
4. Plug;
501. First switch, 502. Second switch;
601. Battery, 602. Charging port.

DETAILED DESCRIPTION OF EMBODIMENTS

The technical solutions of the present disclosure will be clearly and completely described below with reference to the accompanying drawings. Obviously, the described embodiments are part of the embodiments of the present disclosure, rather than all the embodiments. Based on the embodiments of the present disclosure, all other embodiments obtained by those of ordinary skill in the art without creative efforts fall within the scope of protection of the present disclosure.

In the description of the present disclosure, it should be noted that the terms "center", "upper", "lower", "left", "right", "vertical", "horizontal", "inner" and "outer" indicate orientations or positional relationships based on the orientations or positional relationships shown in the drawings. They are only for the convenience of describing the present disclosure and simplifying the description, but not intended to indicate or imply that the device or element referred to must have a specific orientation or must be configured or operated in a specific orientation, therefore they cannot be construed as limitations of the present disclosure. Furthermore, the terms "first", "second" and "third" are used for descriptive purposes only and are not to be construed as indicating or implying relative importance.

In the description of the present disclosure, it should be noted that, unless otherwise clearly stated and limited, the terms "install", "connect" and "link" should be understood in a broad sense. For example, it can be a fixed connection or a removable/detachable connection, or an integral connection; it can be a mechanical connection or an electrical connection; it can be a direct connection or an indirect connection through an intermediate medium; it can be an internal connection between two components. For those of ordinary skill in the art, the specific meanings of the above terms in the present disclosure can be understood according to specific circumstances.

In addition, the technical features involved in different embodiments of the present disclosure described below can be combined with each other as long as they do not conflict with each other.

Figure 2:
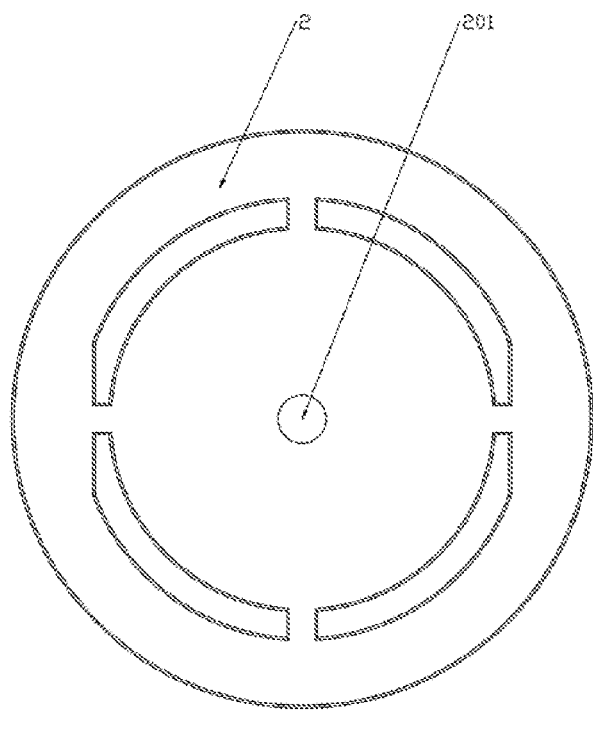
FIG. 2 is a top view of the essential oil spray device of the present disclosure.
Figure 3:
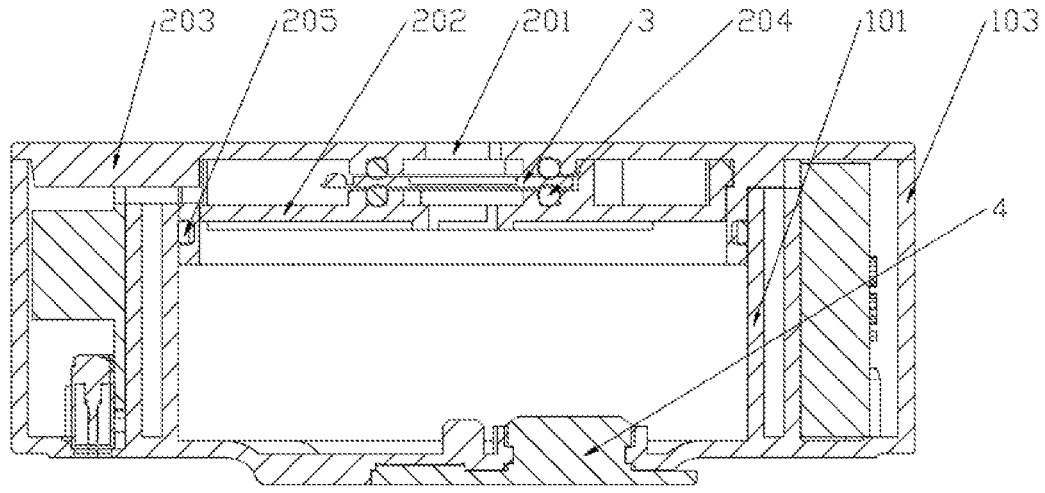
FIG. 3 is a cross-sectional view of the essential oil spray device of the present disclosure.
Figure 4:
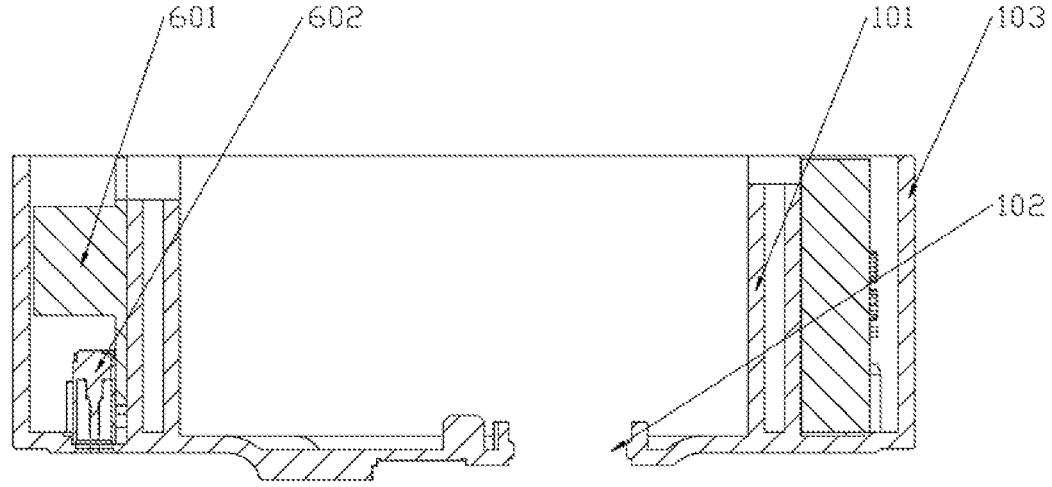
FIG. 4 is a cross-sectional view of the essential oil spray device of the present disclosure with the cover assembly and the plug hidden.
Figure 5:
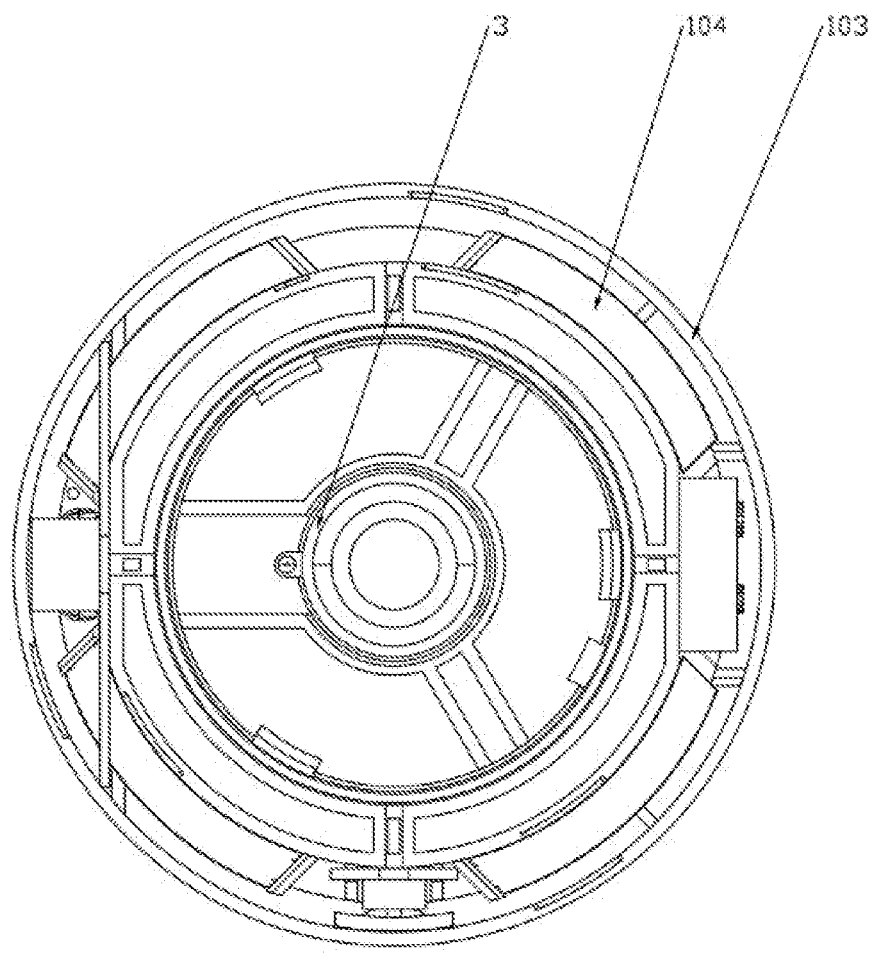
FIG. 5 is a top view of the essential oil spray device of the present disclosure with the outer cover hidden.
Figure 6:
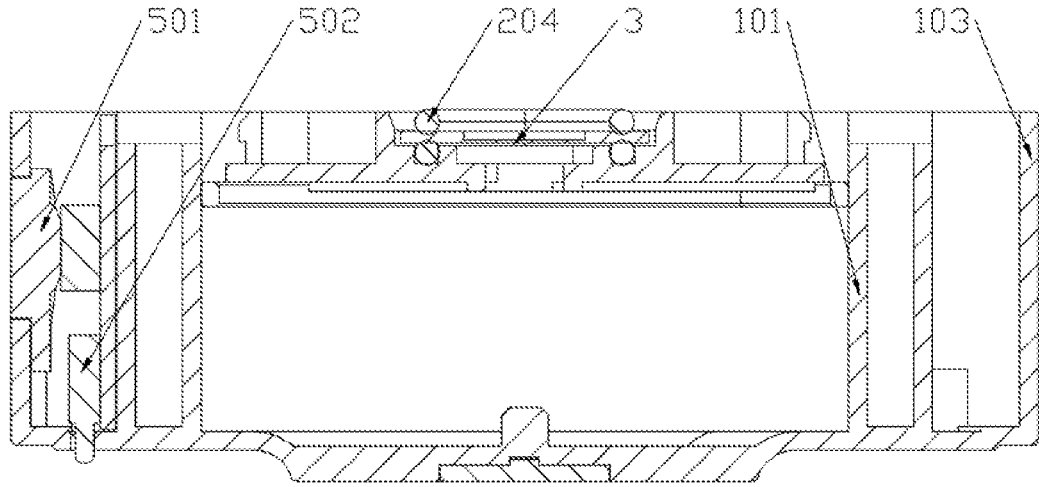
FIG. 6 is a cross-sectional view of the essential oil spray device of the present disclosure with the outer cover hidden.

As shown in FIGS. 1 to 6, it is an optional embodiment of the essential oil spray device of the present disclosure. This essential oil spray device can be installed in a hair dryer, so that the hair dryer can spray essential oil onto the hair while drying the hair, which can provide care for hair. Moreover, this essential oil spray device can replenish the essential oil without replacing the essential oil bottle after the essential oil is used up, thereby reducing the cost of use. The essential oil spray device adopts an integral design with simple structure and small installation space, and is suitable for hair dryers of various sizes.

The above-mentioned essential oil spray device includes a box assembly 1, a cover assembly 2, a plug 4 and a switch assembly. The box assembly 1 includes a liquid storage part 101, the essential oil is filled/placed in the liquid storage part 101. The liquid storage part 101 is provided with a liquid filling port 102 through which the essential oil can be added to the liquid storage part 101. Therefore, after the essential oil in the liquid storage part 101 is used up, it can be added directly, without replacing the entire box assembly 1, and the cost of use is lower. A plug 4 is provided at the liquid filling port 102 for blocking the liquid filling port 102 to prevent essential oil from leaking from the liquid filling port 102 during normal use. The plug 4 is made of fluorosilicone material, the fluorosilicone material will not expand under long-term immersion in the essential oil like ordinary silicone materials, it has good high temperature resistance and can be used under high temperature conditions when the hair dryer blows hot air. The cover assembly 2 is sealingly connected to the liquid storage part 101, the cover assembly 2 is provided with a spray port 201, the spray port 201 is provided with an atomizing member 3, and the atomizing member 3 can atomize the essential oil in the liquid storage part 101 and spray it out from the spray port 201. The switch assembly is arranged on the box assembly 1 and is electrically connected to the atomizing member 3. The switch assembly can control the activation of the atomizing member. By means of the connection of the box assembly 1 and the cover assembly 2 in this essential oil spray device, the overall installation is completed, the overall structure is simple and compact, and it takes up less installation space.

Specifically, in this embodiment, the liquid storage part 101 is approximately cylindrical, that is, one end of the liquid storage part 101 is an open end, and a liquid filling port 102 is provided in the other end. The cover assembly 2 covers the opening end of the liquid storage part 101 to form a closed space for accommodating essential oil. The spray port 201 of the cover assembly 2 faces towards the open end of the liquid storage part 101.

In other embodiments, the liquid storage part 101 may also be in a parallelepiped shape or other shapes, but it is necessary to ensure that the cover assembly 2 and the liquid storage part 101 are completely sealed.

Furthermore, the box assembly 1 further includes a connecting part 103, which is arranged around the outside of the liquid storage part 101 and connected to the liquid storage part 101. In this embodiment, the connecting part 103 is annular, and the connecting part 103 surrounds the outside of the liquid storage part 101. And the connecting part 103 has an annular groove, and the magnetic component 104 is arranged in the annular groove. The magnetic component 104 is preferably magnet, and the number of the magnetic components 104 can be adaptively selected according to the size of the annular groove. In this embodiment, a total of three magnetic components 104 are provided, and it can be connected to the hair dryer through the magnetic components 104. The annular groove of the connecting part 103 and the inside of the liquid storage part 101 are not communicated with each other. There is a passage for air to pass between the connecting part 103 and the liquid storage part 101. When the essential oil spray device is installed on the hair dryer, the wind blown by the hair dryer can be blown out from the passage between the connecting part 103 and the liquid storage part 101. Correspondingly, the cover assembly will also cover the annular groove of the connecting part 103 to prevent dust from entering and accumulating in the annular groove.

Further, the cover assembly 2 includes an inner cover 202 and an outer cover 203. The shape of the outer cover 203 is similar to the shape of the box assembly 1. The portion of the outer cover 203 located above the liquid storage part 101 is sealingly connected to the liquid storage part 101, and a sealing ring 205 is provided at the connection for sealing. The portion of the outer cover 203 located above the connecting part 103 covers the annular groove of the connecting part 103. Moreover, the outer cover 203 is provided with a spray port 201, and the spray port 201 faces towards the liquid storage part 101.

The inner cover 202 is disposed inside the outer cover 203 and connected with the outer cover 203. Specifically, the outer edge of the inner cover is in contact with the inner edge of the outer cover 203, and the inner wall of the outer cover 203 is provided with a clamping slot, the top of the inner cover 202 has a clamping portion, and the clamping portion cooperates with the clamping slot to realize the connection between the inner cover 202 and the outer cover 203.

The atomizing member 3 is disposed between the outer cover 203 and the inner cover 202, and seals 204 are provided on both sides of the atomizing member 3. The outer cover 203 has a first protrusion protruding downward, and a groove is provided in the first protrusion. The inner cover 202 has a second protrusion protruding upward, and a groove is also provided in the second protrusion. The positions of the first protrusion and the second protrusion are opposite (face to each other). The atomizing member 3 is arranged between the first protrusion and the second protrusion, and the two sealing members 204 on both sides of the atomizing member 3 are respectively arranged in the grooves in the first protrusion and the second protrusion. By arranging the sealing ring 205 and the two seals 204, the connection between the box assembly 1 and the cover assembly 2 is completely sealed, which has good sealing performance and can prevent essential oil from leaking.

The switch assembly includes a first switch 501 and a second switch 502 provided on the connecting part 103. The first switch 501 is electrically connected to the second switch 502, and the second switch 502 is electrically connected to the atomizing member 3. Specifically, the first switch 501 is a manual switch, and the second switch 502 is a micro switch. Before using the essential oil spray device, you first need to turn on the micro switch, then the essential oil spray device is in standby mode. Then if pressing the manual switch, the essential oil spray device can spray essential oil. If the micro switch is turned off, the essential oil spray device will not spray essential oil even if the manual switch is pressed. When not in use for a long time, you can turn off the micro switch to reduce the risk of misoperation causing the essential oil spray device to work.

The essential oil spray device also includes a power supply component. The power supply component includes a battery 601 and a charging port 602 arranged in the annular groove of the connecting part 103. The electric energy required for the operation of the atomizing member 3 is provided by the battery 601. The battery 601 can store electricity, the battery 601 can be recharged in time through the charging port 602, so that the essential oil spray device can be used continuously and improve the endurance of the essential oil spray device.

This embodiment also provides a hair dryer. The hair dryer includes a body and an essential oil spray device. The structure of the essential oil spray device is the same as that of the essential oil spray device in the above embodiments, so the details will not be described again.

The essential oil spray device is arranged in the body of the hair dryer, and the spray port 201 faces towards the air outlet side of the body of the hair dryer. The passage between the connecting part 103 and the liquid storage part 101 is along the air outlet direction of the body of the hair dryer. The passage between the connecting part 103 and the liquid storage part 101 can reduce the obstruction effect of the essential oil spray device for the air, prevent the blowing effect of the hair dryer from being weakened, but it can use the wind to blow the spray onto the hair.

Specifically, the essential oil spray device is magnetically connected to the body of the hair dryer through the magnetic component 104 in the connecting part 103 of the box assembly 1. This facilitates the disassembly and assembly of the essential oil spray device and has high adaptability.

The working process of the hair dryer provided in this embodiment is described below:

First, turn on the second switch 502 of the essential oil spray device, and then magnetically attach the essential oil spray device to the body of the hair dryer to complete the installation of the essential oil spray device. Then the hair dryer is turned on to discharge air normally, and then the first switch 501 is turned on. The hair dryer can spray essential oil simultaneously when the air is discharged, and the user can apply the essential oil on the hair for care.

When the essential oil in the essential oil spray device is used up, remove the essential oil spray device, pull out the plug 4, add essential oil from the liquid filling port 102, and then seal the plug 4 at the liquid filling port 102.

Obviously, the above-mentioned embodiments are only examples for clear explanation and are not intended to limit the present disclosure. For those of ordinary skill in the art, other changes or modifications in different forms can be made based on the above description. An exhaustive list of all implementations or embodiments is neither necessary nor possible. The obvious changes or modifications derived therefrom fall within the protection scope of the present disclosure.

What is claimed is:

1. An essential oil spray device, comprising:
a box assembly (1) comprising a liquid storage part (101), a liquid filling port (102) being provided in the liquid storage part (101);
a cover assembly (2), sealingly connected to the liquid storage part (101), the cover assembly (2) being provided with a spray port (201), and the spray port (201) being provided with an atomizing member (3);
a plug (4), provided at the liquid filling port (102);
a switch assembly, provided on the box assembly (1) and electrically connected to the atomizing member (3);
wherein the box assembly (1) further comprises a connecting part (103), and the connecting part (103) is arranged around the liquid storage part (101) and connected with the liquid storage part (101);
wherein the cover assembly (2) comprises an inner cover (202) and an outer cover (203), the outer cover (203) is sealingly connected with the liquid storage part (101), the spray port (201) is provided on the outer cover (203), the inner cover (202) is arranged inside the outer cover (203) and connected with the outer cover (203).

2. The essential oil spray device according to claim 1, wherein the connecting part (103) has an annular groove, and a magnetic component (104) is arranged in the annular groove.

3. The essential oil spray device according to claim 2, further comprising a power supply component, wherein the power supply component comprises a battery (601) and a charging port (602) disposed in the annular groove of the connecting part (103).

4. The essential oil spray device according to claim 1, wherein the atomizing member (3) is provided between the outer cover (203) and the inner cover (202), and the atomizing member (3) is provided with seals (204) on both sides thereof.

5. The essential oil spray device according to claim 1, wherein the switch assembly comprises a first switch (501) and a second switch (502) provided on the connecting part (103), the first switch (501) is electrically connected to the second switch (502), and the second switch (502) is electrically connected to the atomizing member (3).

6. The essential oil spray device according to claim 1, wherein the plug (4) is made of fluorosilicone material.

7. A hair dryer, comprising the essential oil spray device according to claim 1, wherein the essential oil spray device is arranged in a body of the hair dryer, and the spray port (201) faces towards an air-out side of the body of the hair dryer.

8. The hair dryer according to claim 7, wherein the essential oil spray device is magnetically connected to the body of the hair dryer through a magnetic component (104) in the connecting part (103) of the box assembly (1).

\* \* \* \* \*